(12) United States Patent
Weisshaar

(10) Patent No.: US 10,427,112 B2
(45) Date of Patent: Oct. 1, 2019

(54) AERATION DEVICE FOR BIOREACTORS

(75) Inventor: Stefan Weisshaar, Adelebsen (DE)

(73) Assignee: SARTORIUS STEDIM BIOTECH GMBH, Goettingen (DE)

(*) Notice: Subject to any disclaimer, the term of this patent is extended or adjusted under 35 U.S.C. 154(b) by 0 days.

(21) Appl. No.: 13/825,072

(22) PCT Filed: Aug. 6, 2011

(86) PCT No.: PCT/EP2011/003953
§ 371 (c)(1),
(2), (4) Date: Mar. 19, 2013

(87) PCT Pub. No.: WO2012/041416
PCT Pub. Date: Apr. 5, 2012

(65) Prior Publication Data
US 2013/0175716 A1 Jul. 11, 2013

(30) Foreign Application Priority Data

Sep. 30, 2010 (DE) .................. 10 2010 046 989

(51) Int. Cl.
B01F 3/04 (2006.01)
B01F 15/00 (2006.01)
C12M 1/00 (2006.01)

(52) U.S. Cl.
CPC ...... B01F 3/04106 (2013.01); B01F 3/04262 (2013.01); B01F 3/04531 (2013.01);
(Continued)

(58) Field of Classification Search
CPC .. B01F 2003/04148; B01F 2003/04326; B01F 2003/04283; B01F 2003/04354;
(Continued)

(56) References Cited

U.S. PATENT DOCUMENTS 4,207,275 A 6/1980 Stanton, Jr. et al.
4,521,349 A * 6/1985 Weber ................. B01F 3/04262
209/169

(Continued)

FOREIGN PATENT DOCUMENTS

DE 813 995 9/1951
DE 975 813 12/1962
(Continued)

OTHER PUBLICATIONS

"Porous Metal Design Guidebook" published May 2013 accessed at <http://spintek.com/wp-content/uploads/2013/05/porous_metal_membrane_guide_spintek.pdf>.*
(Continued)

Primary Examiner — Stephen Hobson
(74) Attorney, Agent, or Firm — Gerald E. Hespos; Michael J. Porco; Matthew T. Hespos

(57) ABSTRACT

Aeration device for bioreactors with an aeration element with gas outlet openings arranged in a housing, the aeration element taking the form of a microsparger, the gas outlet openings of which are in each case spaced apart from one another and have a size of between 100 μm and 200 μm. At least one second aeration element with gas outlet openings of a second size is preferably provided, the aeration elements being formed by a common housing with separate aeration channels.

15 Claims, 5 Drawing Sheets

(52) U.S. Cl.
CPC ......... *B01F 15/0085* (2013.01); *C12M 29/06* (2013.01); *B01F 2003/04326* (2013.01); *B01F 2003/04361* (2013.01); *B01F 2003/04645* (2013.01); *B01F 2003/04673* (2013.01); *B01F 2215/0404* (2013.01); *B01F 2215/0431* (2013.01)

(58) Field of Classification Search
CPC .. B01F 2003/04361; B01F 2003/04368; B01F 2003/0439; B01F 2003/04297; B01F 3/04106; B01F 3/04262; B01F 3/04248; B01F 2003/04375; B01F 3/04531; B01F 15/0085; B01F 2215/0431; B01F 2003/04673; B01F 2003/04645; B01F 2215/0404; C12M 29/06
USPC ........................................................ 261/124
See application file for complete search history.

(56) References Cited

U.S. PATENT DOCUMENTS

| | | | | |
|---|---|---|---|---|
| 4,888,294 | A * | 12/1989 | Van Wezel | ............ C12M 27/02 435/290.1 |
| 5,858,283 | A * | 1/1999 | Burris | ........................ 261/122.1 |
| 6,338,964 | B1 | 1/2002 | Matanguihan et al. | |
| 2005/0151281 | A1* | 7/2005 | Tharp | ................. B01F 3/04269 261/122.1 |
| 2006/0033222 | A1 | 2/2006 | Godfrey et al. | |
| 2007/0126135 | A1* | 6/2007 | Abello | ................ B01F 3/04269 261/122.1 |
| 2008/0068920 | A1* | 3/2008 | Galliher | .............. B01F 3/04106 366/102 |
| 2009/0129201 | A1* | 5/2009 | Terentiev | ............. B01F 1/0011 366/273 |
| 2010/0015696 | A1* | 1/2010 | Claes | .................. B01F 3/04269 435/303.3 |
| 2011/0013473 | A1 | 1/2011 | Ludwig et al. | |
| 2011/0038222 | A1* | 2/2011 | Ludwig | ............... B01F 3/04269 366/102 |
| 2012/0313267 | A1 | 12/2012 | Pradel et al. | |

FOREIGN PATENT DOCUMENTS

| | | | |
|---|---|---|---|
| DE | 689 09 667 | 2/1994 | |
| DE | 697 09 276 | 8/2002 | |
| EP | 0704237 A2 * | 4/1996 | ........... B01F 3/0412 |
| EP | 0 829 534 | 3/1998 | |
| JP | 01086867 | 3/1989 | |
| WO | 2009/115926 | 9/2009 | |
| WO | 2009/116002 | 9/2009 | |
| WO | WO 2009116002 A1 * | 9/2009 | .......... B01F 3/04269 |
| WO | 2009/122310 | 10/2009 | |
| WO | 2011/057718 | 5/2011 | |
| WO | 2011057718 A1 | 5/2011 | |

OTHER PUBLICATIONS

Translation International Preliminary Report on Patentability.
International Search Report dated Nov. 29, 2011.
European Office Action dated Oct. 4, 2018.

* cited by examiner

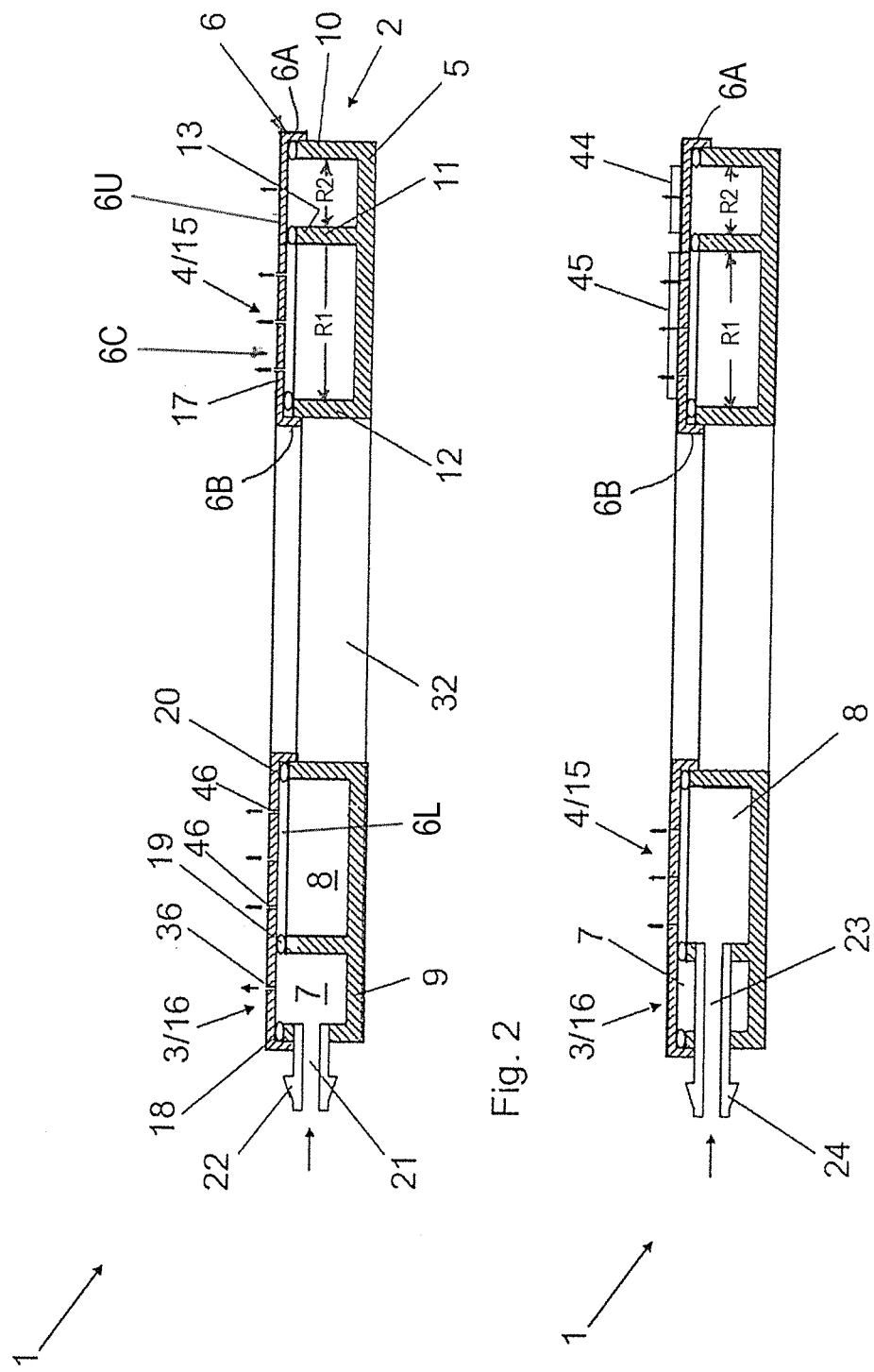

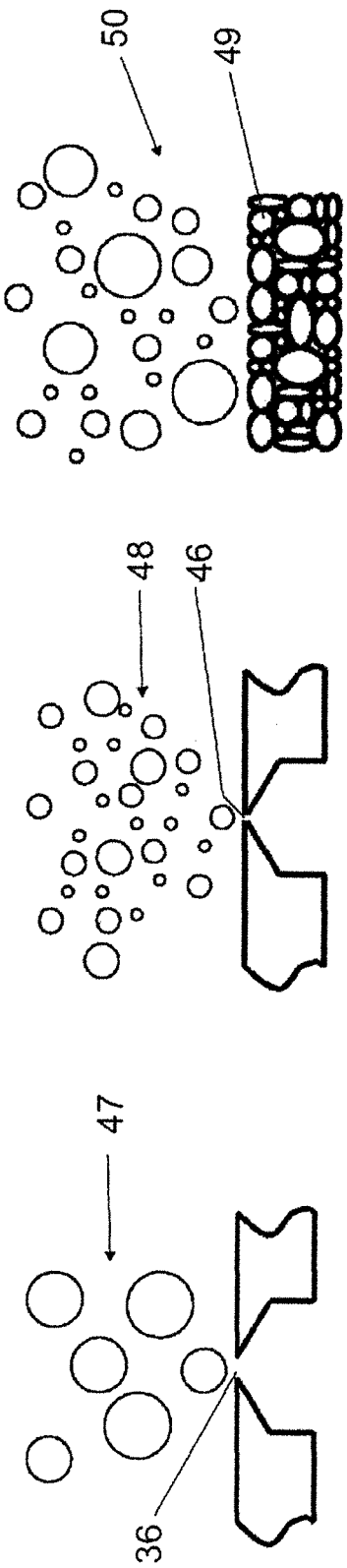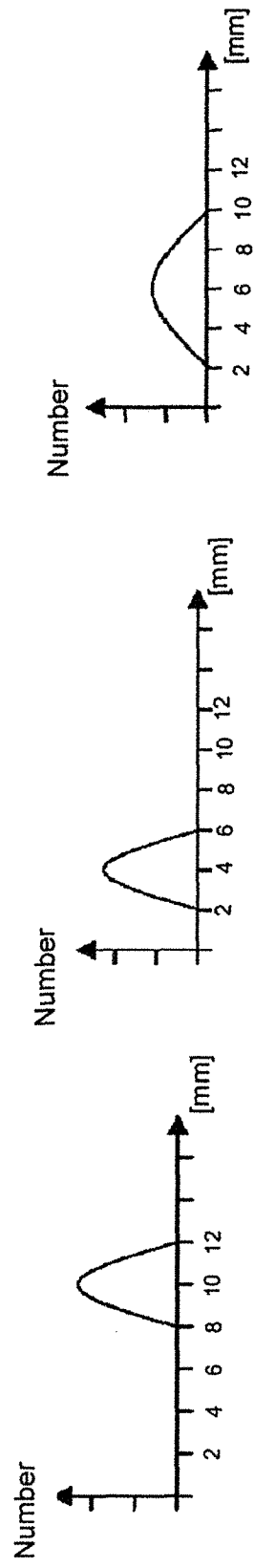
Fig. 4
Fig. 5
Fig. 6
Fig. 7
Fig. 8 (Prior Art)
Fig. 9 (Prior Art)

AERATION DEVICE FOR BIOREACTORS

BACKGROUND

1. Field of the Invention

The invention relates to an aeration device for bioreactors with an aeration element with gas outlet openings.

2. Description of the Related Art

Provision of a gas supply and in particular provision of an oxygen supply is a key factor in cellular metabolic processes. Although animal cell cultures consume substantially less oxygen than bacteria and yeast cultures, ensuring an efficient supply is the greatest challenge facing the operation of a cell culture bioreactor. In addition to supplying the cells with oxygen, the concentration of dissolved carbon dioxide also plays a part as a controlled variable.

There are two conventional aeration methods: aerating the headspace of the bioreactor and direct injection of the gases through aeration rings. For this purpose, use is made not only of the aeration rings known from fermenters with bores or gas outlet openings of for example 0.8 mm but also of "microspargers" made from sintered plastics with pore sizes of for example 20 to 60 µm, which likewise form gas outlet openings. Both kinds have specific advantages and drawbacks.

The aeration ring produces larger bubbles, which means that higher gas throughput rates are required to achieve the same "oxygen transfer rate". With its relatively large bubbles, the ring sparger is suitable for stripping or sweeping out $CO_2$ with air, for example.

With its relatively small bubbles, the microsparger is particularly suitable for supplying oxygen.

One drawback, however, is that under unfavorable conditions foaming may occur due to the relatively small bubbles. Due to the different pore sizes of the sintered material, which inevitably form immediately spaced-apart gas outlet openings with a size of between about 20 and about 70 µm, the microsparger generates gas bubbles in a relatively wide range from about 2 mm to about 10 mm in diameter.

Aeration devices are used as part of automated bioreactor aeration systems, for example single-use reactors, the supply of air, oxygen, carbon dioxide and nitrogen being mutually independently controllable. Sensors for oxygen partial pressure and pH enable the control of these important process parameters.

WO 2009/122310 A2, WO 2009/115926 A2 and WO 2009/116002 A1 disclose single-use bioreactors with a mixer and with an aeration device arranged on the bottom of the reactor interior. It is known here to arrange two aeration elements on the bottom which take the form of opposing, mating ring segments.

Where microspargers are used for this purpose, they exhibit the above-described disadvantages.

The object of the present invention is accordingly to improve known bioreactor aeration devices taking the form of microspargers in such a manner that, while retaining a simple structure, bubble formation of the aeration element taking the form of a microsparger is enabled in a more narrowly and better definable range.

SUMMARY OF THE INVENTION

Said object is achieved in an aeration device for bioreactors in that the aeration element takes the form of a microsparger, the gas outlet openings of which are in each case spaced apart from one another and have a size of between 100 µm and 200 µm.

While in the known use of a porous material which has immediately spaced-apart gas outlet openings of different sizes of between 20 and 60 µm, porous material is not used in the case of the spaced-apart gas outlet openings, such that the gas outlet openings all have the same specified size which may be between 100 µm and 200 µm.

Gas outlet openings with a diameter between 130 µm and 180 µm are here preferred for the microsparger and, according to a further preferred embodiment of the invention, gas outlet openings with a diameter of about 150 µm are used.

Surprisingly to a person skilled in the art, it has been found that gas outlet openings spaced apart from one another with relatively large diameters of about 150 µm are capable of generating gas bubbles in a relatively narrowly defined range of from 2 to 6 mm.

Dispensing with porous material additionally permits considerable simplification of the housing.

According to a further preferred embodiment of the invention, at least one second aeration element with gas outlet openings of a second size is provided, the aeration elements being formed by a common housing with separate aeration channels.

Thanks to the common housing, the aeration device may be arranged simply and centrally relative to a bioreactor mixer while occupying little space.

According to a further preferred embodiment of the invention, the housing takes the form of an annular disk, in which the aeration elements are arranged concentrically.

The concentric arrangement of the aeration elements relative to one another enables an ideal arrangement relative to a mixer or stirrer, which is in turn capable of optimally distributing the gas bubbles in such an arrangement.

According to another preferred embodiment of the invention, the second aeration element takes the form of a sparger or ring sparger, the gas outlet openings of which are in each case spaced apart from one another and have a size of between 600 µm and 1000 µm. The gas outlet openings of the second aeration element which takes the form of a sparger has a size of 800 µm. Gas bubbles with a diameter of between 8 and 12 mm may here be generated.

According to another preferred embodiment of the invention, the housing comprises a lower part, in which are arranged the aeration channels with in each case a radially extending inflow. In this manner, each of the separately arranged aeration channels comprises a dedicated radially extending inflow.

According to a further preferred embodiment of the invention, the lower part is covered by an upper part, which covers the aeration channel of the sparger and the aeration channel of the microsparger and comprises the gas outlet openings of the aeration elements.

The upper part may be sealed relative to the lower part comparatively simply by seals, for example O-ring cord seals or O-rings. The upper part may also be adhesively bonded to the lower part or they may be firmly connected to one another by welding.

According to a further preferred embodiment of the invention, the housing comprises a central opening adjusted to a stirrer flange of the bioreactor and may be arranged upstream of a stirrer on the bottom of an interior of the bioreactor.

Thanks to the central opening of the aeration device, the latter may be positioned optimally relative to a stirrer arranged in the reactor interior.

The volumetric flow rates of the aeration elements may be adapted to the reactor volume by being differently dimensioned. In particular in the case of aeration elements, the number of holes may be adjusted to the volume or effective volume of the reactor. In this manner, a constant bubble size distribution may be achieved combined with any desired scalability of the reactor volume.

Further details of the invention may be inferred from the following detailed description and the attached drawings, which illustrate preferred embodiments of the invention by way of example.

BRIEF DESCRIPTION OF THE DRAWINGS

FIG. 2 is a side view of the aeration device of FIG. 1 sectioned along line II-II.

FIG. 3 is a side view of the aeration device of FIG. 1 sectioned along line III-III.

FIG. 4 is an enlarged side view of a gas outlet opening with a diameter of 800 µm of an aeration element taking the form of a sparger and emerging gas bubbles.

FIG. 5 is a diagram of the number of gas bubbles as a function of the size (diameter) thereof according to FIG. 4.

FIG. 6 is an enlarged side view of a gas outlet opening with a diameter of 150 µm of an aeration element taking the form of a sparger and emerging gas bubbles.

FIG. 7 is a diagram of the number of gas bubbles as a function of the size (diameter) thereof according to FIG. 6.

FIG. 8 is an enlarged side view of gas outlet openings with diameters of between 20 and 60 µm of an aeration element taking the form of a microsparger with a porous material according to the prior art and emerging gas bubbles.

FIG. 9 is a diagram of the number of gas bubbles as a function of the size (diameter) thereof according to FIG. 8 (prior art).

DETAILED DESCRIPTION OF THE PREFERRED EMBODIMENTS

Figure 1:
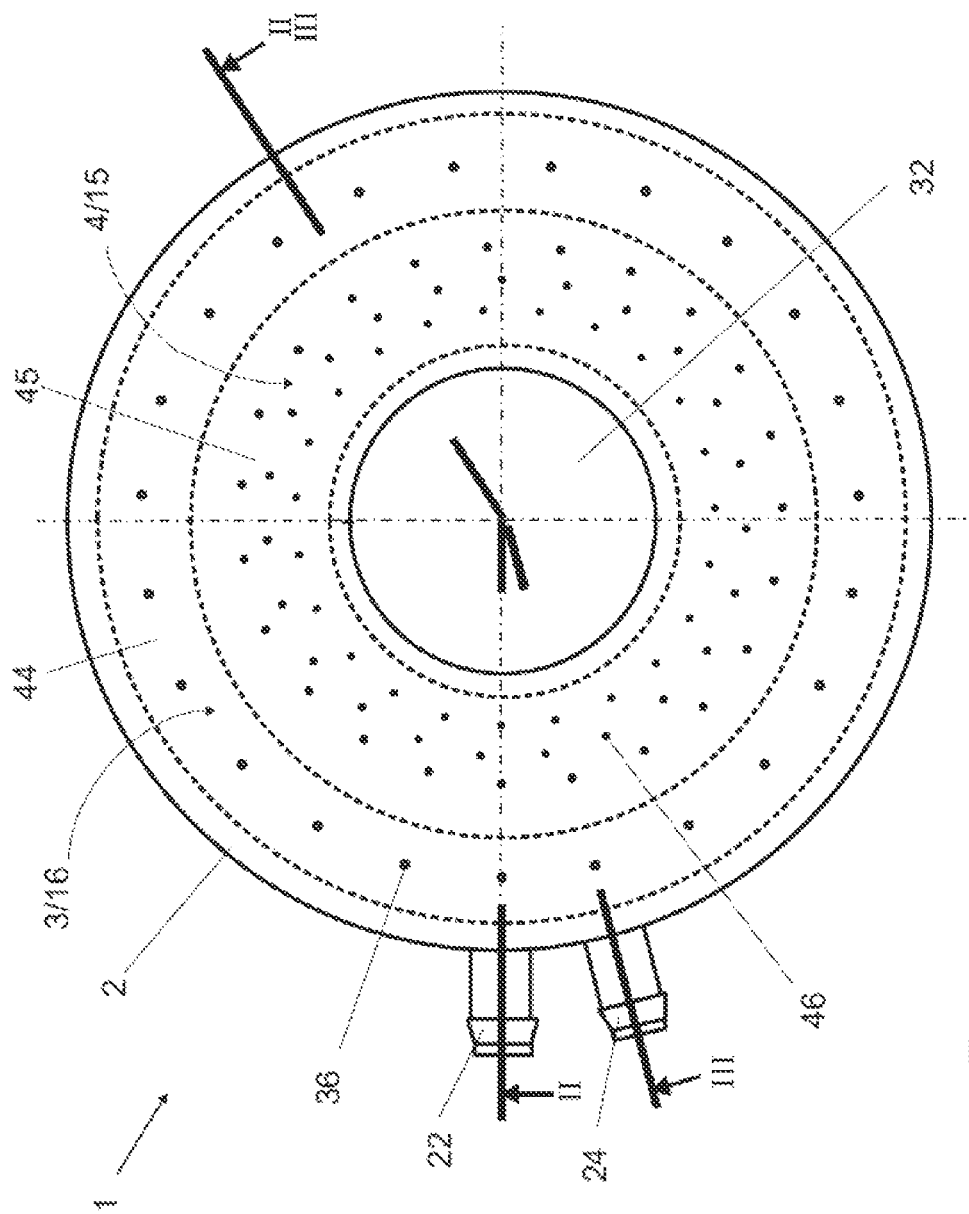
FIG. 1 is an enlarged plan view of a medium-sized aeration device.

An aeration device 1 substantially consists of a housing 2 with a (first) aeration element 4 and a second aeration element 3.

The housing 2 consists of a lower part 5 and an upper part 6 positionable on the lower part 5. The lower part 5 comprises two aeration channels 7, 8 arranged concentrically to one another. The aeration channels 7, 8 are downwardly delimited in the vertical direction by a bottom 9 of the lower part 5. The second aeration channel 7 is laterally delimited by the outer wall 10 and, toward the first aeration channel 8, by a partition wall 11. The first aeration channel 8 is correspondingly delimited towards the second aeration channel 7 by the partition wall 11 and, on the side thereof remote from the second aeration channel 7, by an inner wall 12 of the lower part 5. The first aeration channel 8 defines a radial dimension R1 between the partition wall 11 and the inner wall 12 that exceeds a radial dimension R2 of the second aeration channel 7 between the outer wall 10 and the partition wall 1, as shown in FIGS. 2 and 3.

The upper part 6 positionable on the lower part 5 closes the second aeration channel 7 with a second annular region 44 and forms therewith the second aeration element 3. More particularly, the upper part 6 has an outer flange 6A that engages an upper region of an outer surface of the outer wall 10, an inner flange 6B that engages an upper region of an inner surface of the inner wall 12 and an upper wall 6C extending between the outer and inner flanges 6A and 6B, as shown in FIGS. 2 and 3. The upper wall 6C has upper and lower surfaces 6U and 6L. To this end, the upper part 6 comprises outer gas outlet openings 36 in the second annular region 44 thereof, the diameter of which gas outlet openings 36 in each case amounts to about 800 µm. The second aeration element 3 consequently forms a "ring sparger" or sparger 16.

FIG. 4 shows an enlarged view of a gas outlet opening 36 of a sparger 16 with emerging gas bubbles 47. FIG. 5 shows the distribution of different sizes (8 to 12 mm) of the gas bubbles 47. The y-axis indicates the number and the x-axis the size.

The upper part 6 closes the first aeration channel 8 with a first annular region 45 and forms therewith the first aeration element 4. To this end, the upper part 6 comprises inner gas outlet openings 46 in the first annular region 45 thereof, the diameter of which gas outlet openings in each case amounts to about 150 µm. The first aeration element 4 consequently forms a "microsparger" 15.

FIG. 6 shows an enlarged view of a gas outlet opening 46 of a microsparger 15 with emerging gas bubbles 48. FIG. 7 shows the distribution of different sizes (2 to 6 mm) of the gas bubbles 48. The y-axis indicates the number and the x-axis the size.

FIG. 8 shows an enlarged view of gas outlet openings of a microsparger with a porous material 49 known from the prior art with emerging gas bubbles 50. FIG. 9 shows the distribution of different sizes (2 to 10 mm) of the gas bubbles 50. The y-axis indicates the number and the x-axis the size.

Sealing between the lower part 5 and upper part 6 is provided by in each case arranging seals 18, 19, 20, which take the form of O-ring cord seals or O-rings, on the walls 10, 11, 12.

The second aeration channel 7 comprises a radially extending second inflow 21 which leads into a tube connection 22. The first aeration channel 8 correspondingly comprises a first radially extending inflow 23 which leads into a tube connection 24. Nonreturn valves (not shown) may be arranged in the tube connections 22, 24 or in the inflows 21, 23.

Figure 10:
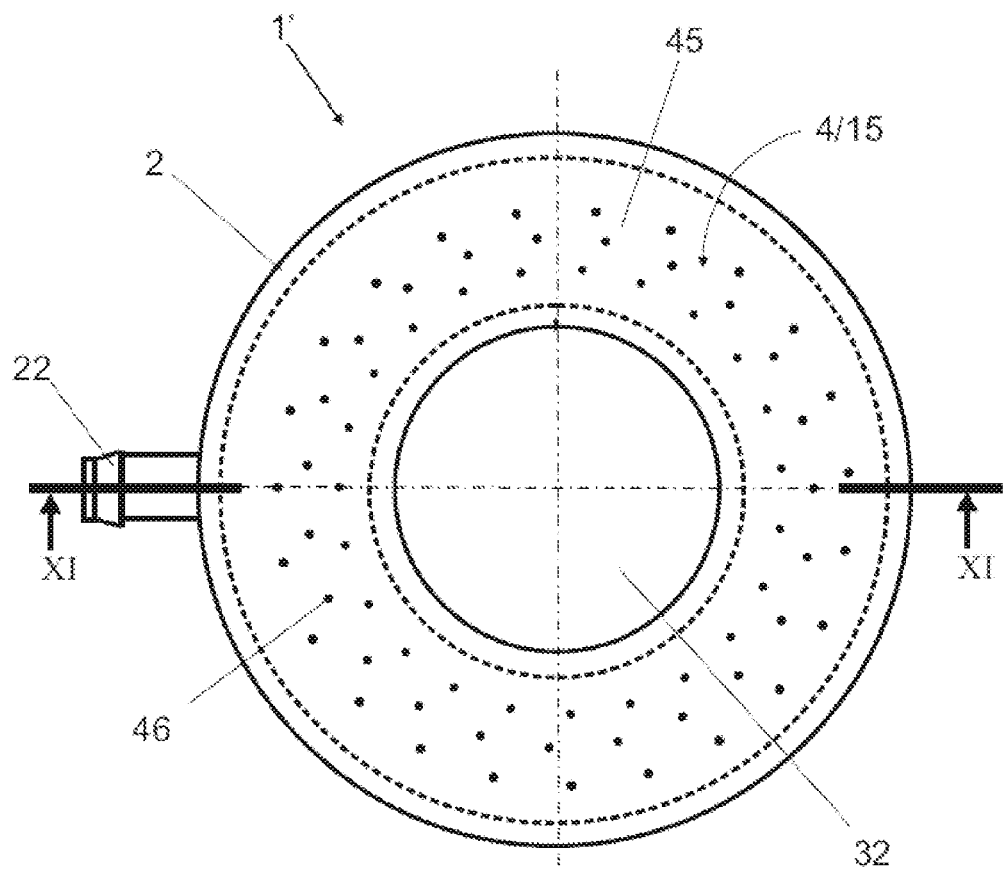
FIG. 10 is an enlarged plan view of an aeration device taking the form of a microsparger.
Figure 11:
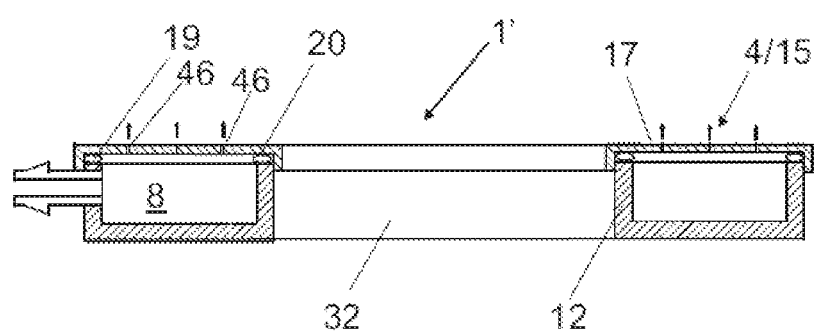
FIG. 11 is a side view of the aeration device of FIG. 10 sectioned along line XI-XI.

FIGS. 10 and 11 show an aeration device 1' taking the form of a microsparger 15.

Figure 12:
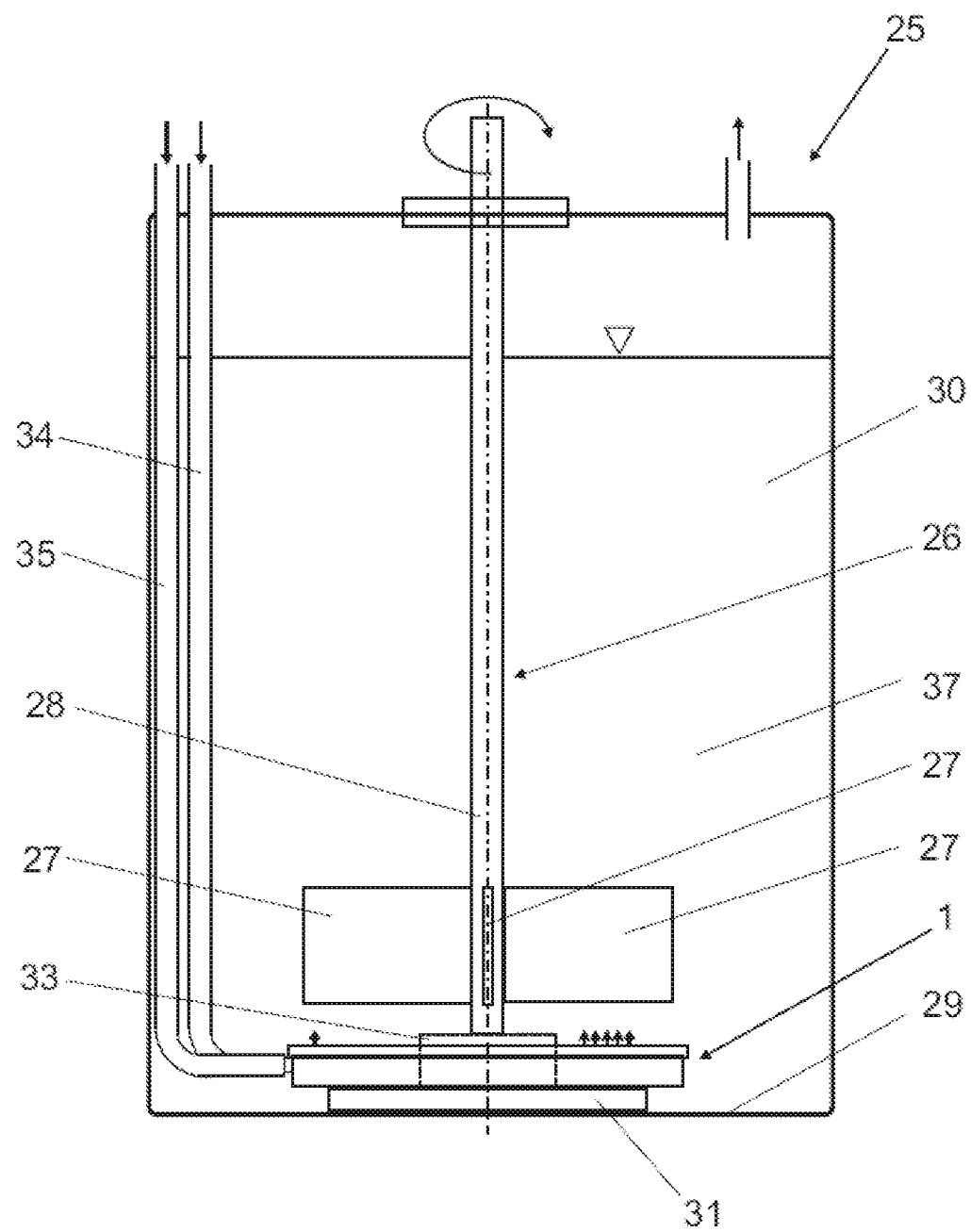
FIG. 12 is a side view of a bioreactor with stirrer and an aeration device.

FIG. 12 shows by way of example a bioreactor 25, which for example takes the form of a flexible pouch for single use and comprises a stirrer 26, which may be driven from outside, with stirrer blades 27. The bioreactor 25 comprises an interior 30, on the bottom 29 of which is arranged a stirrer flange 31. The stirrer shaft 28 is mounted rotatably in the stirrer flange 31. The aeration device 1 is pushed with its central opening 32 onto a shoulder 33 of the stirrer flange 31. Gas is supplied via a second inflow line 34 to the second inflow 21 and via a first inflow line 35 to the first inflow 23, which gas emerges from the aeration device 1 and forms bubbles in the liquid medium 37 in the interior 30.

Further inflows and outflows and open- and closed-loop control devices are not shown.

The invention claimed is:

1. An aeration device for a bioreactor (25), comprising:
a lower part (5) having an annular bottom wall (9), an outer circumferential wall (10) projecting up from the bottom wall (9), an inner circumferential wall (12) concentric with the outer circumferential wall (10) and projecting up from the bottom wall (9) and a circumferentially extending partition wall (11) concentric with the outer and inner circumferential walls (10, 12) and projecting up from the bottom wall (9) at a position between the outer and inner circumferential walls (10, 12) so that an outer aeration channel (7) is defined between the outer circumferential wall (10) and the partition wall (11) and an inner aeration channel (8) is defined between the partition wall (11) and the inner circumferential wall (12); and
an upper part (6) mounted to ends of the outer and inner circumferential walls (10, 12) and the partition wall (11) and opposed to the bottom wall (9) to define a housing (2) with the upper part (6) covering both the outer aeration channel (7) and the inner aeration channel (8), the upper part (6) having a lower surface facing into the outer aeration channel (7) and the inner aeration channel (8) and an upper surface opposite the lower surface, areas of the upper part (6) that cover the outer aeration channel (7) being formed with outer gas outlet openings (36) that are arranged circumferentially at equal intervals, each of the outer gas outlet openings (36) extending from the lower surface to the upper surface, all of the outer gas outlet openings (36) being spaced apart from one another at all locations on each outer gas outlet opening (36) from the lower surface to the upper surface and having a cross-sectional dimension at the upper surface that is the same for all of the outer gas outlet openings (36) and areas of the upper part (6) that cover the inner aeration channel (8) being formed with inner gas outlet openings (46) extending from the lower surface to the upper surface, minimum spacings between the inner gas outlet openings (46) being less than the intervals between the outer gas outlet openings (36), all of the inner gas outlet openings (46) being spaced apart from one another at all locations on each inner gas outlet opening (46) from the lower surface to the upper surface and having a cross-sectional dimension at the upper surface that is the same for all of the inner gas outlet openings (46) and that is different than the cross-sectional dimension of outer gas outlet openings (36), wherein the same cross-sectional dimension for all of the outer gas outlet openings (36) achieves a specified distribution of bubble sizes from the outer gas outlet openings (36) and the same cross-sectional dimension for all of the inner gas outlet openings (46) achieves a specified distribution of bubble sizes from the inner gas outlet openings (46) that is different from the specified distribution of bubble sizes from the outer gas outlet openings (36), the cross-sectional dimensions of the outer gas outlet openings (36) being at least three times the cross-sectional dimensions of the inner gas outlet openings (46).

2. The aeration device of claim 1, wherein
the housing (2) comprises a central opening (32) dimensioned to receive a stirrer flange (31) of the bioreactor (25) arranged upstream of a stirrer (26) and on a bottom (29) of an interior (30) of the bioreactor (25).

3. The aeration device of claim 1, wherein the same size for the inner gas outlet openings (46) is a selected same size of between 100 µm and 200 µm.

4. The aeration device of claim 3, wherein the same size for the outer gas outlet openings (36) is a selected same size of between 600 µm and 1000 µm.

5. The aeration device of claim 1, further comprising a first gas inflow line (21) extending radially through the outer circumferential wall (10) of the lower part (5) and communicating with the outer aeration channel (7) and a second gas inflow line (23) extending radially through the outer circumferential wall (10) and through the partition wall (11) of the lower part (5) and communicating with the inner aeration channel (8).

6. The aeration device of claim 1, further comprising seals (18, 19, 20) between the upper part (6) and the outer and inner circumferential walls (10, 12) and the partition wall (11).

7. The aeration device of claim 1, wherein the upper part (6) has opposite upper and lower surfaces, the outer gas outlet openings (36) of the first size and the inner gas outlet openings (46) of the second size being adjacent the upper surface and widening to larger sizes at positions closer to the lower surface of the upper part (6).

8. The aeration device of claim 1, wherein the upper part (6) has an outer circumferential flange that engages an upper region of an outer surface of the outer circumferential wall (10) and an inner circumferential flange that engages an upper region of an inner surface of the inner circumferential wall (12).

9. The aeration device of claim 1, wherein each of the first and second gas outlet openings (46, 36) extends substantially perpendicularly from the lower surface to the upper surface of the upper part (6).

10. An aeration device for a bioreactor (25), comprising:
a lower part (5) having an annular bottom wall (9), an outer circumferential wall (10) projecting up from the bottom wall (9), an inner circumferential wall (12) concentric with the outer circumferential wall (10) and projecting up from the bottom wall (9) and a circumferentially extending partition wall (11) concentric with the outer and inner circumferential walls (10, 12) and projecting up from the bottom wall (9) at a position between the outer and inner circumferential walls 10, 12) so that an outer aeration channel (7) is defined between the outer circumferential wall (10) and the partition wall (11) and an inner aeration channel (8) is defined between the partition wall (11) and the inner circumferential wall 12); and
an upper part (6) mounted to ends of the outer and inner circumferential walls (10, 12) and the partition wall (11) and opposed to the bottom wall (9) to define a housing (2) with the upper part (6) covering both the outer aeration channel (7) and the inner aeration channel (8), the upper part (6) having a lower surface facing into the outer aeration channel (7) and the inner aeration channel (8) and an upper surface opposite the lower surface, areas of the upper part (6) that cover the outer aeration channel (7) being formed with outer gas outlet openings (36) extending from the lower surface to the upper surface, all of the outer gas outlet openings (36) being spaced apart from one another at all locations on each outer gas outlet opening (36) from the lower surface to the upper surface and having a cross-sectional dimension at the upper surface that is the same for all of the outer gas outlet openings (36) and areas of the upper part (6) that cover the inner aeration channel (8) being formed with inner gas outlet openings (46) extending from the lower surface to the upper surface, all of the inner gas outlet openings (46) being spaced apart from one another at all locations on each inner gas outlet opening (46) from the lower surface to the upper surface and having a cross-sectional dimension at the upper surface that is the same for all of the inner gas outlet openings (46) and that is different than the cross-sectional dimension of outer gas outlet openings (36), wherein the same cross-sectional dimension for all of the outer gas outlet openings (36) achieves a specified distribution of bubble sizes from the outer gas outlet openings (36) and the same cross-sectional dimension for all of the inner gas outlet openings (46) achieves a specified distribution of bubble sizes from the inner gas outlet openings (46) that is different from the specified distribution of bubble sizes from the outer gas outlet openings (36), the cross-sectional dimensions of the outer gas outlet openings (36) being at least three times the cross-sectional dimensions of the inner gas outlet openings (46), wherein each of the inner and outer gas outlet openings (46, 36) is wider adjacent the lower surface of the upper part (6) than adjacent the upper surface of the upper part (6).

11. The aeration device of claim 10, wherein
the same size that is the same for all of the inner gas outlet openings (46) is a selected same size that is between 130 μm and 180 μm.

12. The aeration device of claim 10, wherein
the same size that is the same for all of the inner gas outlet openings (46) is 150 μm.

13. The aeration device of claim 10, wherein
the same size for the outer gas outlet openings (36) is 800 μm.

14. The aeration device of claim 10, wherein the second gas outlet openings (36) are arranged circumferentially at equal intervals.

15. The aeration device of claim 14, wherein minimum spacings between the first gas outlet openings (46) are less than the intervals between the second gas outlet openings (36).

* * * * *